US00PP25473P2

(12) United States Plant Patent
Geers

(10) Patent No.: US PP25,473 P2
(45) Date of Patent: Apr. 28, 2015

(54) ***EXOCHORDA* PLANT NAMED 'SNOW MOUNTAIN'**

(50) Latin Name: *Exochorda×racemosa*
Varietal Denomination: Snow Mountain

(71) Applicant: Herman Geers, Boskoop (NL)

(72) Inventor: Herman Geers, Boskoop (NL)

( * ) Notice: Subject to any disclaimer, the term of this patent is extended or adjusted under 35 U.S.C. 154(b) by 170 days.

(21) Appl. No.: 13/986,770

(22) Filed: Jun. 4, 2013

Related U.S. Application Data

(60) Provisional application No. 61/849,921, filed on Feb. 5, 2013.

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Annette Para
(74) *Attorney, Agent, or Firm* — Penny J. Aguirre

(57) ABSTRACT

A new cultivar of *Exochorda*, 'Snow Mountain', that is characterized by its floriferous habit with flowers present the entire length of the stem, its upright and compact plant habit, its ability to be readily propagated by softwood stem cutting with good rooting, its consistent growth habit, and its healthy, disease free foliage.

2 Drawing Sheets

Botanical classification: *Exochorda×racemosa.*
Variety denomination: 'Snow Mountain'.

BACKGROUND OF THE INVENTION

The present invention relates to a new and distinct cultivar of *Exochorda racemosa*. The new cultivar will be referred to hereafter by its cultivar name, 'Snow Mountain'. 'Snow Mountain' is a new cultivar of deciduous shrub grown for use as a landscape shrub.

The new cultivar is a selection from a controlled breeding program conducted by the Inventor at his nursery in Boskoop, The Netherlands with the goal of selecting new cultivars of *Exochorda* with better flowering characteristics, easier propagation, and good garden performance.

The new variety of *Exochorda* was selected by the Inventor amongst seedlings derived from a cross made in 1994 between 'The Bride' (not patented) as the female parent and an unnamed plant of *Exochorda racemosa* from the Inventor's breeding program. 'Snow Mountain' was selected as a single unique plant in 1997.

Asexual propagation of the new cultivar was first accomplished by the Inventor by softwood stem cuttings in Boskoop, The Netherlands in 1998. Asexual propagation by softwood stem cuttings has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Snow Mountain' as a unique cultivar of *Exochorda.*

1. 'Snow Mountain' exhibits a floriferous habit with flowers present the entire length of the stem.
2. 'Snow Mountain' exhibits an upright and compact plant habit.

3. 'Snow Mountain' is readily propagated by softwood stem cuttings with good rooting.
4. 'Snow Mountain' has been shown to be a consistent grower.
5. 'Snow Mountain' exhibits healthy disease free foliage.

The female parent 'Snow Mountain', 'The Bride', differs from 'Snow Mountain' in having a mounded plant habit with arching branches with flowering not extending to the base of the branches, in being more difficult to root. The male parent, an unnamed plant of *Exochorda racemosa*, differs from 'Snow Mountain' in being much taller and less compact and having inconsistent flowering. 'Snow Mountain' can also be compared to the cultivar 'The Pearl' (a hybrid of *E. racemosa* and *E. giraldii* var. *wilsonii*). 'The Pearl' is similar to 'Snow Mountain' in having stems with dense blooms dense, however 'The Pearl' differs from 'Snow Mountain' in having larger flowers and in being much taller in height.

BRIEF DESCRIPTION OF THE DRAWING

The accompanying colored photographs illustrate the overall appearance and distinct characteristics of the new cultivar. The photographs were taken of a two year-old plant of the new cultivar as grown outdoors in a field in Boskoop, The Netherlands.

The photograph in FIG. 1 provides a view of the plant habit and flowering habit of 'Snow Mountain'.

Figure 1:
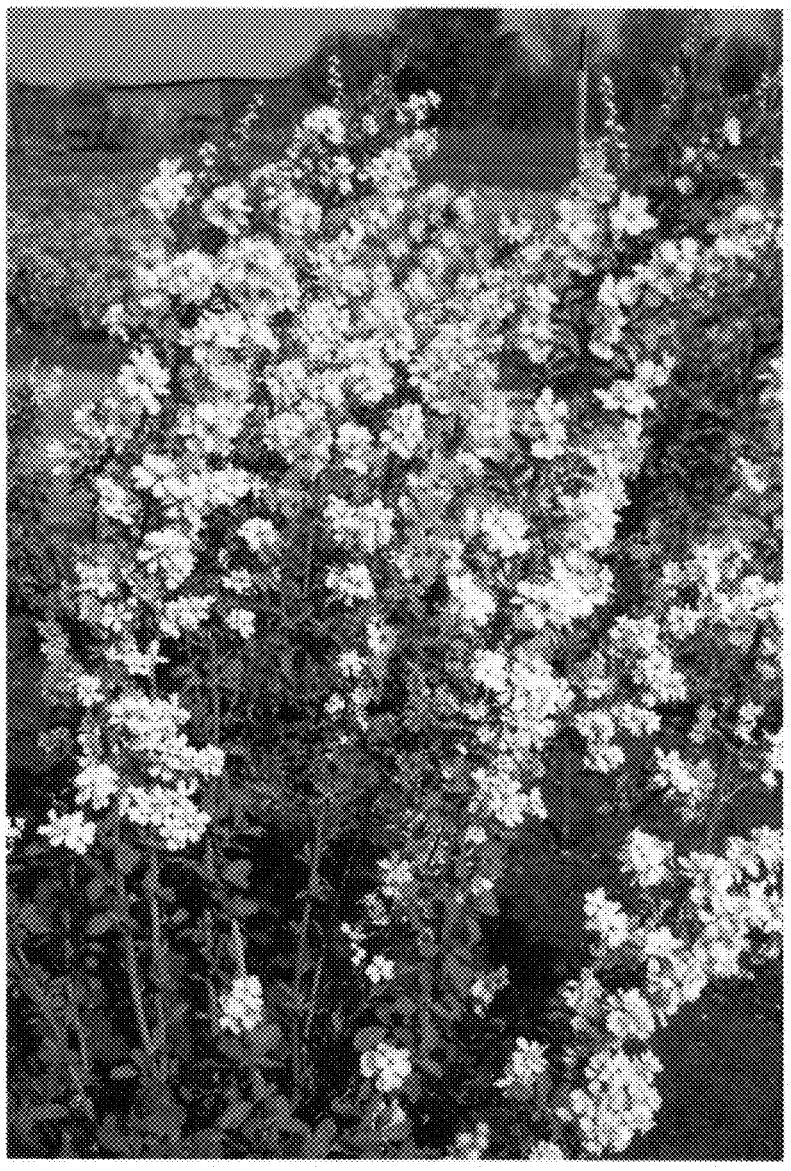
Figure 2:
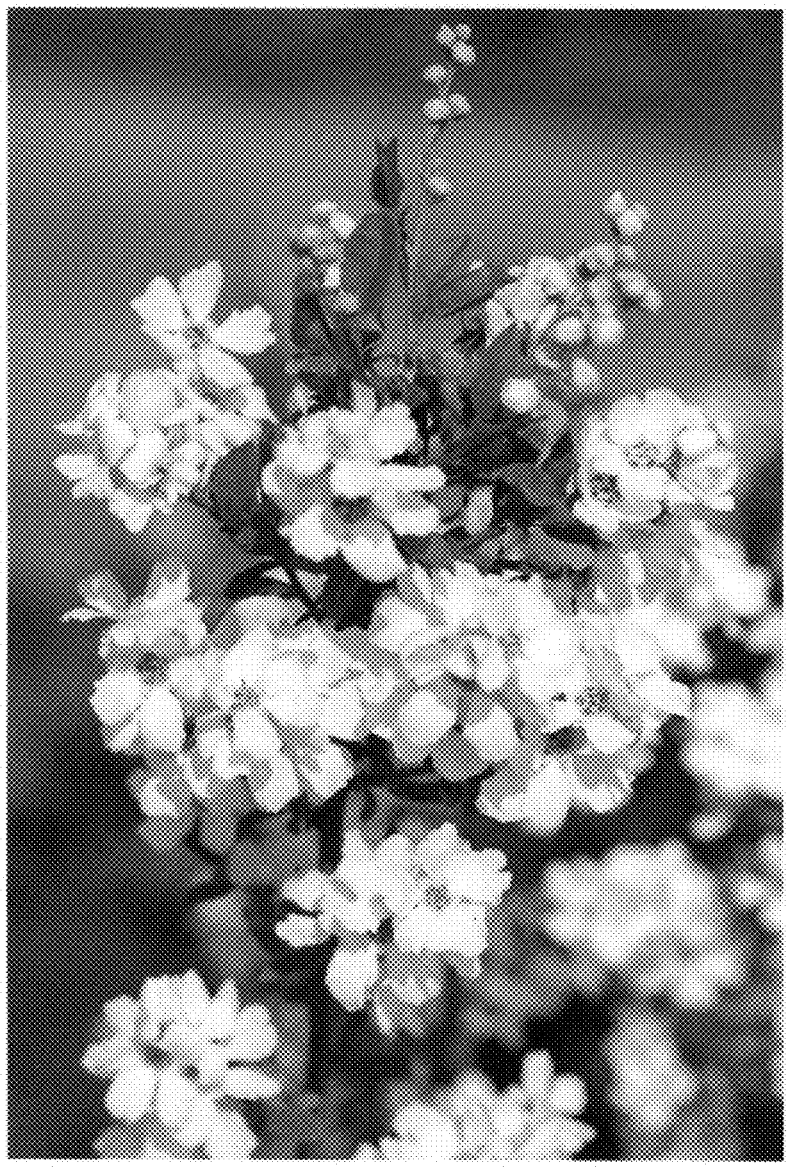

The photograph in FIG. 2 provides a close-up view of the flowers of 'Snow Mountain'.

The colors in the photographs are as close as possible with digital photography techniques available, the color values cited in the detailed botanical description accurately describe the colors of the new *Exochorda.*

DETAILED BOTANICAL DESCRIPTION

The following is a detailed description of two year-old plants of the new cultivar as field grown in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for 2 to 3 weeks in spring in Boskoop, The Netherlands.

*Plant habit.*—Compact in comparison to plants of the species, upright.

*Height and spread.*—1.6 m in height and spread.

*Cold hardiness.*—At least to U.S.D.A. Zone 5.

*Diseases.*—Has been observed to be disease free under the conditions tested.

*Propagation.*—Easily propagated by softwood stem cuttings good rooting rate.

*Growth.*—Moderate.

*Roots.*—Fleshy when young plants, becoming fibrous on mature plants.

Branch description:

*Stem color.*—Young; 145A, maturing; 166A, mature; 177D.

*Stem surface.*—Young and mature; smooth.

*Branching.*—4 to 5 basal branches.

*Stem size.*—Ranges from 1 to 2 cm in width, average of 1.6 m in length.

Foliage description:

*Leaves.*—Simple, oblong in shape, arrangement is alternate, average of 4 cm in length and 3 cm in width, apex acute to apiculate, base cuneate, margin entire, internode length is an average of 4 cm, attachment petiolate, color of new growth upper and lower surface 148A, color when mature upper and lower surface 138A, venation pinnate with midribs N144A and other veins matching leaf in color, surface smooth on upper and lower surface.

*Petioles.*—Range from 4 mm to 2.5 cm in length, an average of 2 mm in diameter, 145A in color, surface smooth.

Inflorescence description:

*Inflorescence type.*—Racemes at nodes from top of stem to the base.

*Inflorescence size.*—4 to 7 cm in length and an average of 4 cm in diameter.

*Inflorescence number.*—30 per stem.

*Flower number.*—Average of 5 to 12 per raceme.

*Flower fragrance.*—None.

*Flower longevity.*—About 14 days.

*Flower type.*—Single, rotate.

*Flower size.*—3 to 4 cm in diameter and 5 mm in depth.

*Peduncles.*—3 to 8 mm in length and 0.2 mm in diameter, 145A in color, surface is smooth.

*Flower buds.*—Globose in shape, 4 to 7 mm in length and width, 157C in color.

*Sepals.*—5, oval in shape, margin entire, color of upper and lower surface 157A, average of 2 cm in length and width, acute apex, cuneate base, smooth surface.

*Petals.*—5, round in shape, upper surface and lower surface is smooth, margin irregularly notched, base cuneate, apex is rounded with small notch, average of 2 cm in length and width, color: opening and fully open flowers upper and lower surface; NN155A .

Reproductive organs:

*Pistils.*—1, stigma is an average of 5 mm in length and 1 mm in width and 1C in color, style is an average of 3 mm in length and 1C in color, ovary is egg-shaped, 2 mm in length, 3 mm in width and 1B in color.

*Stamens.*—About 20, filaments are about 3 mm in length and 1C in color, anthers are an average of 1.5 mm in length and 0.5 mm in width and 151B in color, pollen is moderate in quantity and 8B in color.

*Fruit.*—Capsule; 5-valved, an average of 1 cm in length and 1.5 cm in diameter, surface is smooth, 199D in color, seeds; N199B in color.

It is claimed:

1. A new and distinct cultivar *Exochorda* plant named 'Snow Mountain' as herein illustrated and described.

* * * * *